(12) United States Patent
Van Duren (10) Patent No.: US 9,068,895 B2
(45) Date of Patent: Jun. 30, 2015

(54) DEEP TISSUE TEMPERATURE PROBE CONSTRUCTIONS

(75) Inventor: Albert P. Van Duren, Chaska, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1413 days.

(21) Appl. No.: 12/798,946

(22) Filed: Apr. 14, 2010

(65) Prior Publication Data

US 2010/0268114 A1 Oct. 21, 2010

Related U.S. Application Data (60) Provisional application No. 61/212,704, filed on Apr. 15, 2009.

(51) Int. Cl.
| | | |
|---|---|---|
| *A61B 5/00* | (2006.01) | |
| *G01K 1/16* | (2006.01) | |
| *A61B 5/01* | (2006.01) | |
| *G01K 13/00* | (2006.01) | |

(52) U.S. Cl.
CPC . *G01K 1/165* (2013.01); *A61B 5/01* (2013.01); *A61B 5/6833* (2013.01); *A61B 2562/0271* (2013.01); *A61B 2562/0276* (2013.01); *A61B 2562/164* (2013.01); *G01K 1/16* (2013.01); *G01K 13/002* (2013.01)

(58) Field of Classification Search
CPC .. A61B 5/01; A61B 5/6833; A61B 2562/164; A61B 2562/0276; G01K 13/002; G01K 1/16; G01K 1/165

USPC ............ 324/158, 750.03; 600/549; 374/163, 374/183
See application file for complete search history.

(56) References Cited

U.S. PATENT DOCUMENTS

| | | | |
|---|---|---|---|
| 1,363,259 A | 12/1920 | Mills | |
| 1,526,641 A | 2/1925 | Mulvany et al. | |
| 1,528,383 A | 3/1925 | Schmidt | |
| 1,638,943 A | 8/1927 | Little | |
| 2,378,804 A | 6/1945 | Sparrow et al. | |
| 2,381,819 A | 8/1945 | Graves et al. | |
| 2,519,785 A | 8/1950 | Okolicsanyi | |
| 2,629,757 A | 2/1953 | McKay | |
| 2,807,657 A | 9/1957 | Jenkins et al. | 136/4 |
| 2,969,141 A | 1/1961 | Katzin | 206/16.5 |
| 3,099,575 A | 7/1963 | Hill | 117/212 |

(Continued)

FOREIGN PATENT DOCUMENTS

| | | | | |
|---|---|---|---|---|
| CA | 2 538 940 A1 | 6/2006 | | A61B 5/00 |
| CA | 2 583 034 A1 | 9/2007 | | A61B 5/01 |

(Continued)

OTHER PUBLICATIONS

International Search Report and Written Opinion, PCT/US2011/000549, mailed Jun. 26, 2011.

(Continued)

*Primary Examiner* — Rene Towa
(74) *Attorney, Agent, or Firm* — X. Christina Huang (57) ABSTRACT

A disposable, zero-heat-flux, deep tissue temperature probe is constructed using a support assembly with multiple sections folded together or separated into strata during assembly of the probe. The sections support elements of the probe, including thermal sensors and a thermal resistor between the thermal sensors. Optionally, one of the sections supports a heater.

20 Claims, 7 Drawing Sheets

(56) References Cited

U.S. PATENT DOCUMENTS

| | | | | |
|---|---|---|---|---|
| 3,099,923 | A | 8/1963 | Benzinger | 73/341 |
| 3,215,265 | A | 11/1965 | Welin-Berger | 206/63.2 |
| 3,235,063 | A | 2/1966 | Jarund | 206/16.5 |
| 3,238,775 | A | 3/1966 | Watts | 73/190 |
| 3,301,394 | A | 1/1967 | Baermann et al. | 206/63.2 |
| 3,367,182 | A | 2/1968 | Baxter | 73/190 |
| 3,427,209 | A | 2/1969 | Hager, Jr. | 136/225 |
| 3,469,685 | A | 9/1969 | Baermann | 206/63.2 |
| 3,552,558 | A | 1/1971 | Poncy | 206/63.2 |
| 3,581,570 | A | 6/1971 | Wortz | 73/355 R |
| 3,607,445 | A | 9/1971 | Hines | 136/225 |
| 3,720,103 | A | 3/1973 | Adams et al. | 73/190 H |
| 3,767,470 | A | 10/1973 | Hines | 136/225 |
| 3,781,749 | A | 12/1973 | Iles et al. | 338/25 |
| 3,809,230 | A | 5/1974 | Poncy | 206/306 |
| 3,833,115 | A | 9/1974 | Schapker | 206/63.2 |
| 3,877,463 | A | 4/1975 | Cary et al. | 128/2 H |
| 3,933,045 | A | 1/1976 | Fox et al. | 73/359 |
| 3,942,123 | A | 3/1976 | Georgi | 328/1 |
| 4,022,063 | A | 5/1977 | West et al. | 73/362 |
| 4,024,312 | A | 5/1977 | Korpman | 428/343 |
| 4,142,631 | A | 3/1979 | Brandriff | 206/306 |
| 4,253,469 | A | 3/1981 | Aslan | 128/736 |
| 4,275,741 | A | 6/1981 | Edrich | 128/653 |
| 4,347,854 | A | 9/1982 | Gosline et al. | 128/736 |
| 4,407,292 | A | 10/1983 | Edrich | 128/653 |
| 4,494,550 | A | 1/1985 | Blazek et al. | 128/664 |
| 4,539,994 | A | 9/1985 | Baumbach et al. | 128/635 |
| 4,541,734 | A | 9/1985 | Ishizaka | 374/169 |
| 4,572,213 | A | 2/1986 | Kawahara | 128/736 |
| 4,574,359 | A | 3/1986 | Ishizaka et al. | 364/557 |
| 4,577,976 | A | 3/1986 | Hayashi et al. | 374/29 |
| 4,592,000 | A | 5/1986 | Ishizaka et al. | 364/557 |
| 4,629,336 | A | 12/1986 | Ishizaka | 364/557 |
| 4,648,055 | A | 3/1987 | Ishizaka et al. | 364/557 |
| 4,652,145 | A | 3/1987 | Bjornberg | 374/194 |
| 4,669,049 | A | 5/1987 | Kosednar et al. | 364/557 |
| 4,747,413 | A * | 5/1988 | Bloch | 600/549 |
| 4,841,543 | A | 6/1989 | Dittmar et al. | 374/44 |
| 4,859,078 | A | 8/1989 | Bowman et al. | 374/44 |
| 4,899,297 | A | 2/1990 | Sano et al. | 364/557 |
| 4,955,380 | A | 9/1990 | Edell | 128/635 |
| 4,987,579 | A | 1/1991 | Yoshinaka et al. | 377/25 |
| 5,002,057 | A | 3/1991 | Brady | 128/652 |
| 5,015,102 | A | 5/1991 | Yamaguchi | 374/102 |
| 5,033,866 | A | 7/1991 | Kehl et al. | 374/179 |
| 5,040,901 | A | 8/1991 | Suzuki | 374/183 |
| 5,050,612 | A | 9/1991 | Matsumura | 128/670 |
| 5,062,432 | A | 11/1991 | James et al. | 128/736 |
| 5,088,837 | A | 2/1992 | Shiokawa et al. | 374/185 |
| 5,149,200 | A | 9/1992 | Shiokawa et al. | 374/185 |
| 5,172,979 | A | 12/1992 | Barkley et al. | 374/147 |
| 5,178,468 | A | 1/1993 | Shiokawa et al. | 374/185 |
| 5,199,436 | A | 4/1993 | Pompei et al. | 128/664 |
| 5,255,979 | A | 10/1993 | Ferrari | 374/158 |
| 5,263,775 | A | 11/1993 | Smith et al. | 374/134 |
| 5,293,877 | A | 3/1994 | O'Hara et al. | 128/736 |
| 5,483,190 | A | 1/1996 | McGivern | 327/34 |
| 5,516,581 | A | 5/1996 | Kreckel et al. | 428/317.3 |
| 5,816,706 | A | 10/1998 | Heikkila et al. | 374/134 |
| 5,884,235 | A | 3/1999 | Ebert | 702/87 |
| 5,990,412 | A | 11/1999 | Terrell | 136/225 |
| 5,993,698 | A | 11/1999 | Frentzel et al. | 252/511 |
| 6,001,471 | A | 12/1999 | Bries et al. | 428/343 |
| 6,014,890 | A | 1/2000 | Breen | 73/29.02 |
| 6,019,507 | A | 2/2000 | Takaki | 374/161 |
| 6,059,452 | A | 5/2000 | Smith et al. | 374/169 |
| 6,203,191 | B1 | 3/2001 | Mongan | 374/43 |
| 6,220,750 | B1 * | 4/2001 | Palti | 374/164 |
| 6,224,543 | B1 | 5/2001 | Gammons et al. | 600/124 |
| 6,231,962 | B1 | 5/2001 | Bries et al. | 428/317.3 |
| 6,253,098 | B1 | 6/2001 | Walker et al. | 600/344 |
| 6,255,622 | B1 | 7/2001 | May et al. | 219/209 |
| 6,278,051 | B1 | 8/2001 | Peabody | 136/225 |
| 6,280,397 | B1 | 8/2001 | Yarden et al. | 600/549 |
| 6,283,632 | B1 | 9/2001 | Takaki | 374/161 |
| 6,292,685 | B1 | 9/2001 | Pompei | 600/474 |
| 6,312,391 | B1 | 11/2001 | Ramadhyani et al. | 600/549 |
| 6,355,916 | B1 | 3/2002 | Siefert | 219/494 |
| 6,377,848 | B1 | 4/2002 | Garde et al. | 604/20 |
| 6,398,727 | B1 | 6/2002 | Bui et al. | 600/300 |
| 6,495,806 | B2 | 12/2002 | Siefert | 219/494 |
| 6,553,243 | B2 | 4/2003 | Gurley | 600/340 |
| 6,595,929 | B2 | 7/2003 | Stivoric et al. | 600/549 |
| 6,676,287 | B1 | 1/2004 | Mathis et al. | 374/1 |
| 6,773,405 | B2 | 8/2004 | Fraden et al. | 600/549 |
| 6,776,817 | B2 * | 8/2004 | Lentz et al. | 73/204.26 |
| 6,827,487 | B2 | 12/2004 | Baumbach | 374/164 |
| 6,886,978 | B2 | 5/2005 | Tokita et al. | 374/169 |
| 6,929,611 | B2 | 8/2005 | Koch | 600/549 |
| 7,059,767 | B2 | 6/2006 | Tokita et al. | 374/163 |
| 7,270,476 | B2 | 9/2007 | Tokita et al. | 374/107 |
| 7,299,090 | B2 | 11/2007 | Koch | 600/547 |
| 7,306,283 | B2 | 12/2007 | Howick et al. | 297/180.12 |
| 7,318,004 | B2 | 1/2008 | Butterfield | 702/130 |
| 7,354,195 | B2 | 4/2008 | Sakano | 374/208 |
| 7,364,356 | B2 | 4/2008 | Dicks et al. | 374/121 |
| 7,410,291 | B2 | 8/2008 | Koch | 374/163 |
| 7,426,872 | B2 | 9/2008 | Dittmar et al. | 73/818 |
| 2001/0002918 | A1 * | 6/2001 | Tatoh | 374/179 |
| 2002/0097775 | A1 | 7/2002 | Hamouda et al. | 374/29 |
| 2003/0130590 | A1 | 7/2003 | Bui et al. | 600/537 |
| 2004/0210280 | A1 | 10/2004 | Liedtke | 607/96 |
| 2005/0040510 | A1 * | 2/2005 | Hashimoto | 257/686 |
| 2005/0177063 | A1 * | 8/2005 | Winnie | 600/549 |
| 2005/0245839 | A1 | 11/2005 | Stivoric et al. | 600/549 |
| 2007/0167859 | A1 | 7/2007 | Finneran et al. | 600/546 |
| 2007/0206655 | A1 | 9/2007 | Haslett et al. | 374/141 |
| 2007/0282218 | A1 | 12/2007 | Yarden | 600/549 |
| 2008/0170600 | A1 | 7/2008 | Sattler et al. | 374/163 |
| 2009/0129433 | A1 | 5/2009 | Zhang et al. | 374/102 |
| 2009/0306536 | A1 * | 12/2009 | Ranganathan et al. | 600/549 |
| 2010/0292605 | A1 | 11/2010 | Grassl et al. | 600/549 |

FOREIGN PATENT DOCUMENTS

| | | | | |
|---|---|---|---|---|
| DE | 3527942 | A1 | 2/1987 | G01K 7/00 |
| DE | 10 2006012338 | | 7/2007 | |
| EP | 0239824 | B1 | 5/1992 | G01K 13/00 |
| GB | 2266771 | A | 11/1993 | G01K 1/18 |
| JP | 55-29794 | | 3/1980 | G01K 1/16 |
| JP | 57-183832 | | 12/1982 | A61B 5/00 |
| JP | H08-211000 | | 8/1996 | G01N 25/00 |
| JP | 2002202205 | A | 7/2002 | G01K 7/00 |
| JP | 2007-212407 | A | 8/2007 | A61B 5/01 |
| JP | 2009-080000 | A | 4/2009 | A61B 5/04 |
| WO | WO 99/60356 | A1 | 11/1999 | G01K 17/00 |
| WO | WO 00/58702 | A1 | 10/2000 | G01K 7/02 |
| WO | WO 01/31305 | A1 | 5/2001 | G01K 7/42 |
| WO | WO 02/066946 | A2 | 8/2002 | G01K 13/00 |
| WO | WO 2007/060609 | A2 | 5/2007 | A61B 5/0408 |
| WO | WO 2008/068665 | A1 | 6/2008 | G01K 1/16 |
| WO | WO 2008/078271 | A1 | 7/2008 | G01K 1/16 |
| WO | WO 2009/141780 | A1 | 11/2009 | G01K 1/16 |
| WO | WO 2010/082102 | A2 | 7/2010 | G01K 1/14 |
| WO | WO 2010/103436 | A1 | 9/2010 | G01K 1/16 |
| WO | WO 2010/116297 | A1 | 10/2010 | G01K 1/14 |
| WO | WO 2010/120360 | A1 | 10/2010 | G01K 13/00 |
| WO | WO 2010/120362 | A1 | 10/2010 | G01K 13/00 |
| WO | WO 2011/025521 | A1 | 10/2010 | G01K 1/16 |
| WO | WO 2011/126543 | A1 | 10/2011 | G01K 13/00 |
| WO | WO 2011/146098 | A1 | 11/2011 | G01K 1/16 |

OTHER PUBLICATIONS

International Search Report and Written Opinion, PCT/US2011/000552, mailed Jun. 29, 2011.

Fox RH, et al, A new technique for monitoring the deep body temperature in man from the intact skin surface. *J. Physiol.* 1971; 212(2): 8P-10P.

Solman AJ, et al, New thermometers for deep tissue temperature. *Biomedical Engineering* 1973; 8(10): 432-435.

Fox RH, et al, A new method for monitoring deep body temperature from the skin surface. *Clin. Sci.* 1973; 44: 81-86.

(56) References Cited

OTHER PUBLICATIONS

Togawa, T, et al, A modified internal temperature measurement device, *Medical and Biological Engineering*, May 1976, pp. 361-364.

Togawa T, Non-invasive deep body temperature measurement. In: Rolfe P (ed) *Non-invasive Physiological Measurements*. 1979; vol. 1: 261-277.

Zhang X, et al, Application of the Heat Flux Meter in Physiological Studies, *J. therm. Biol.*, 1993, vol. 18: 473-476. Yamakage M, et al, Deep temperature monitoring-comparative study between conventional and new developed monitors, *Anesthesiology*, 2002; 96: A501.

Suleman M-I, et al, Insufficiency in a new temporal-artery thermometer for adult and pediatric patients, *Anesth Analg*, 2002; 95: 67-71.

Yamakage M, Evaluation of a newly developed monitor of deep body temperature, *J. Anesth.*, 2002; 16:354-357.

Thurbide, K., Excuse me, but my Band-Aid is beeping, Haslett's smart Band-Aid/University of Calgary, Jul. 18, 2007, pp. 1-2.

Gunga H-C, et al, A non-invasive device to continuously determine heat strain in humans. *J. Ther. Bio.* 2008; 33: 297-307.

Kimberger O, Accuracy and precision of a novel non-invasive core thermometer. *BJA*. 2009; 103(2): 226-231.

Langham GE, et al, Noninvasive temperature monitoring in postanesthesia care units, *Anesthesiology*, 2009, 111; 1:1-7.

Kitamura, K, et al, Development of a new method for the noninvasive measurement of deep body temperature without a heater, *Med. Eng. Phys.*, 2010; 32(1): 1-6. Epub Nov. 10, 2009.

Zeiner A, et al, Non-invasive continuous cerebral temperature monitoring in patients treated with mild therapeutic hypothermia: an observational pilot study, *Resuscitation*, Jul. 2010; 81(7) 861-866. Epub Apr. 15, 2010.

International Search Report and Written Opinion, PCT/US2010/001108, mailed Jul. 23, 2010.

International Search Report and Written Opinion, PCT/US2010/001104, mailed Jul. 26, 2010.

International Search Report and Written Opinion, PCT/US2010/002185, mailed Dec. 13, 2010.

\* cited by examiner

DEEP TISSUE TEMPERATURE PROBE CONSTRUCTIONS

PRIORITY

This application claims priority to co-pending U.S. Provisional Application for Patent 61/212,704 filed Apr. 15, 2009.

RELATED APPLICATION

This application contains material related to material disclosed, illustrated, and/or claimed in the following co-pending US patent applications:
U.S. patent application Ser. No. 12/584,108, filed Aug. 31, 2009.

BACKGROUND

The subject matter relates to a temperature probe—a device placed on the skin of a subject to measure temperature. More particularly, the subject matter pertains to a deep tissue temperature (DTT) probe. Deep tissue temperature measurement is a non-invasive determination of the core temperature of a human body in which a probe is located over a region of deep tissue that is representative of the body core. The probe reads the temperature of that region as the core temperature.

A system for non-invasively measuring deep tissue temperature was described by Fox and Solman in 1971 (Fox R H, Solman A J. A new technique for monitoring the deep body temperature in man from the intact skin surface. J. Physiol. January 1971:212(2): pp 8-10). The system, illustrated in the schematic diagram of FIG. 1, estimates body core temperature by indirect means using a specially designed probe that is placed upon the skin of a subject to stop or significantly neutralize heat flow through a portion of the skin in order to measure temperature. The components of the probe 10 are contained in a housing 11. The Fox/Solman probe 10 includes two thermistors 20 mounted on either side of a thermal resistance 22, which may be constituted of a layer of insulating material capable of supporting the thermistors 20. The probe 10 also includes a heater 24 disposed at the top of the probe 10, over the elements 20, 22, and 24. In use, the probe 10 is placed on a region of the skin of a person whose deep tissue temperature is to be measured. With the bottom surface 26 of the probe resting on a person's body, in contact with the skin, the thermistors 20 measure a temperature difference, or error signal, across the thermal resistance 22. The error signal is used to drive a heater controller 30, which, in turn, operates to minimize the error signal by causing the heater 24 to provide just enough heat to equalize the temperature on both sides of the thermal resistance 22. When the temperatures sensed by the thermistors 20 are equal or nearly so, there is no heat flow through the probe, and the temperature measured by the lower thermistor 20 by way of a temperature meter circuit constituted of an amplifier 36 and a temperature meter 38 is equivalent to DTT. The probe 10 essentially acts as a thermal insulator that blocks heat flow through the thermal resistor 22; DTT probes that operate in the same manner are termed "zero-heat-flux" ("ZHF") probes. Since the heater 24 operates to guard against loss of heat along the path of measurement through the probe, it is often referred to as a "guard heater".

Figure 2:
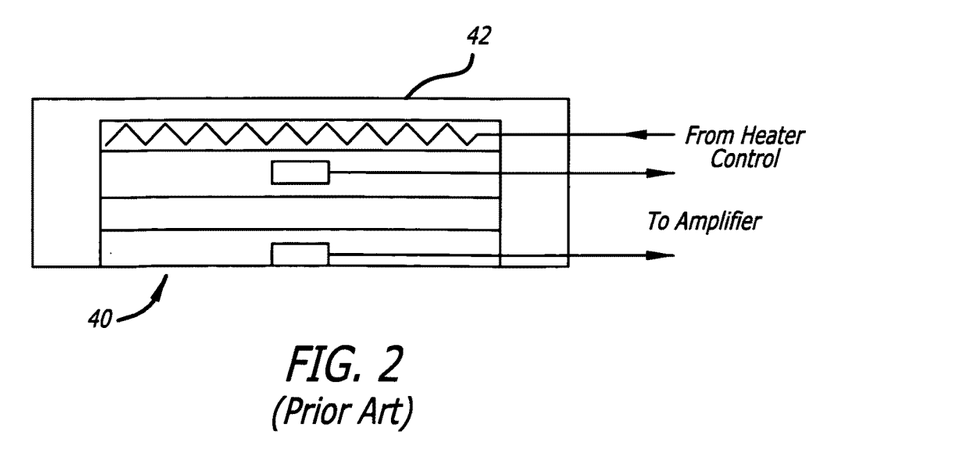
FIG. 2 is a schematic side sectional diagram of a second prior art deep tissue temperature measurement system including a ZHF deep tissue temperature probe with an aluminum cap.

Togawa improved the Fox/Solman design with a DTT probe structure that accounted for the strong multi-dimensional heat transfer of dermal blood flow through the skin. (Togawa T. Non-Invasive Deep Body Temperature Measurement. In: Rolfe P (ed) Non-Invasive Physiological Measurements. Vol. 1. 1979. Academic Press, London, pp. 261-277). The probe, illustrated in FIG. 2, encloses a ZHF sensor design 40, which blocks heat flow normal to the body, in a thick aluminum housing 42 with a disk-like construction that also reduces or eliminates radial heat flow from the center to the periphery of the probe.

ZHF deep tissue temperature measurement were improved in several ways, principally by decreasing the size and mass of a DTT probe to improve response and equilibrium times, and also by adding guard heating around the periphery of the probe to minimize radial heat losses. Nevertheless, ZHF probes have typically been expensive and non-disposable, and have not been widely adopted for clinical use, except for cardiac surgery in Japan. The sensors cannot be effectively heat sterilized, although they can be disinfected with a cold bactericidal solution.

Presently, ZHF probes based on the original Fox and Solman design comprise both software and hardware improvements. One such ZHF probe has a stacked planar structure that consists of a number of discrete layers. An advantage of this design is a narrow width, which helps minimize radial temperature differences from heat loss through the sides of the sensor. This probe includes an optimally-damped heater controller which is operated by use of a PID (Proportional-Integral-Derivative) scheme to maintain the heater temperature just slightly higher than the temperature of the skin. The small temperature difference provides an error signal for the controller. While the hardware design is not disposable, it does provide some basic improvements to the size and mass of the Fox/Solman and Togawa designs.

Maintenance of body core temperature in a normothermic range during a perioperative cycle has been shown to reduce the incidence of surgical site infection, and so it is beneficial to monitor a patient's body core temperature before, during, and after surgery. Of course non-invasive measurement is very desirable, for both the comfort and the safety of a patient. Deep tissue temperature measurement using a probe supported on the skin provides an accurate and non-invasive means for monitoring body core temperature. However, the size and mass of the Fox/Solman and Togawa probes do not promote disposability. Consequently, they must be sterilized after each use, and stored for reuse. As a result, use of these probes to measure deep tissue temperature may raise the costs associated with DTT measurement and may increase the risk of cross contamination between patients. It is therefore useful to reduce the size and mass of a DTT probe, without sacrificing its performance, so as to promote disposability.

SUMMARY OF THE INVENTION

Disposable, zero-heat-flux, deep tissue temperature probes are constructed using a support assembly constituted of a flexible substrate that supports elements of the probe. The support assembly has multiple sections that may be folded together and/or separated to form a multi-level ZHF structure. The sections support elements of the probe, including thermal sensors separated by a layer of thermal resistance interposed between adjacent sensor-supporting sections. Preferably, at least one of the sections supports a heater.

DETAILED DESCRIPTION OF THE PREFERRED EMBODIMENTS

It is desirable that zero-heat-flux, deep tissue temperature probe (DTT probe) constructions be disposable. Thus the constructions should be easy and inexpensive to fabricate and assemble, have a low mass and a low profile, and comprise inexpensive materials and parts.

It is particularly desirable that disposable DTT constructions be assembled from low-profile, light weight, flexible assemblies that enable zero-heat-flux measurement at various locations on a human or animal body.

A thermal measurement support assembly for zero-heat-flux deep tissue temperature probe (DTT probe) constructions includes a flexible substrate with at least two thermal sensors disposed in a spaced-apart relationship and separated by one or more layers of thermally insulating material. Preferably the sensors are spaced apart vertically as in FIGS. 1 and 2, and they may further be spaced apart horizontally or radially with respect to a center of measurement of vertical heat flux. The substrate supports at least the thermal sensors and the separating thermal insulating material, and it may also support one or more heaters. Once constructed, the support assembly is ready to be incorporated into the structure of a DTT probe.

Figure 3:
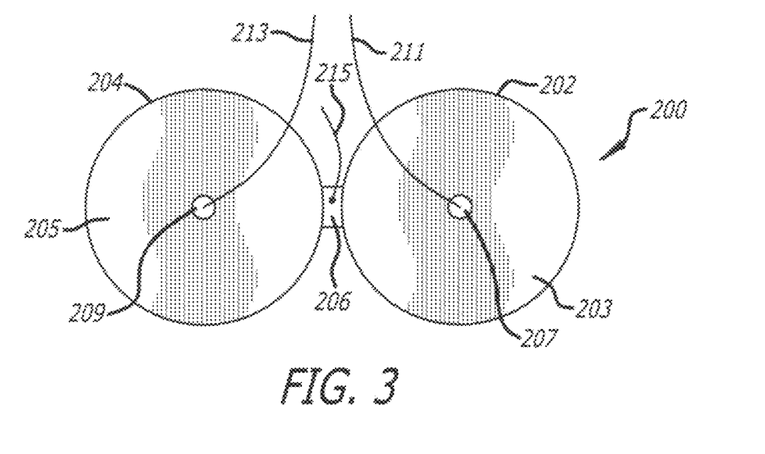
FIG. 3 illustrates a thermal measurement support assembly embodiment for a ZHF probe constituted of a film of material including two sections joined by a hinge.
Figure 4:
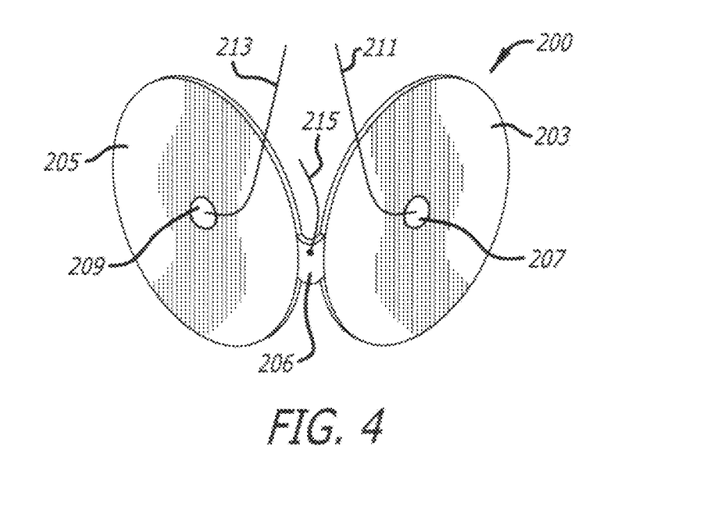
FIG. 4 illustrates the first embodiment with the two sections folded toward each other.
Figure 5:
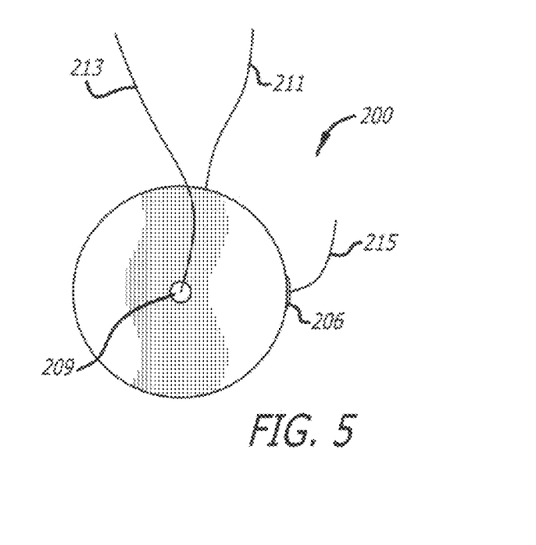
FIG. 5 illustrates the first embodiment with the two sections folded together.

A first embodiment of a support assembly for a DTT probe is illustrated in FIG. 3. The support assembly 200 includes a permanent heater (not shown) with an attachment mechanism (not shown) and is designed and manufactured to be disposable. The support assembly 200 includes a film of material coated with copper on both sides and fashioned into two disk-shaped sections 202 and 204 that are joined at a common peripheral location 206 disposed between the two sections. The disk shaped sections 202 and 204 include major supporting surfaces 203 and 205 respectively. The surfaces on the opposite sides of the major supporting surfaces 203, 205 (which are not seen in these figures) support respective thermocouples whose junctions 207, 209 are visible at the respective centers of the major supporting surfaces 203, 205. Signal leads 211, 213 are connected to the thermocouples at the junctions 207, 209, and a common lead 215 is electrically coupled to the thermocouples. Preferably, a pressure-sensitive adhesive (PSA)-backed, 0.001 inch thick piece of insulative material such as a polyimide layer (Kapton® film, for example) is disposed on one of the surfaces on the opposite side of one of the major supporting surfaces 203, 205, and the support assembly may be folded like a clam shell, on a crease at the common peripheral location 206, as shown in FIGS. 4 and 5. An insulating material with greater thermal resistance may also be interposed between the surfaces 203 and 205 to decrease the sensitivity of the support assembly. When the support assembly is so folded, the thermocouples are disposed in a stacked configuration, with the layer of insulative material disposed therebetween to provide thermal resistance. The copper disks are electrically continuous; therefore, the junction of each thermocouple is common to both disks, which makes it possible to eliminate one wire from the pair of thermocouples. Although the probe is designed to minimize radial heat losses and radial temperature differences, the placement of the thermocouples in the center of the copper disks minimizes fin effects that tend to reduce accuracy.

Figure 1:
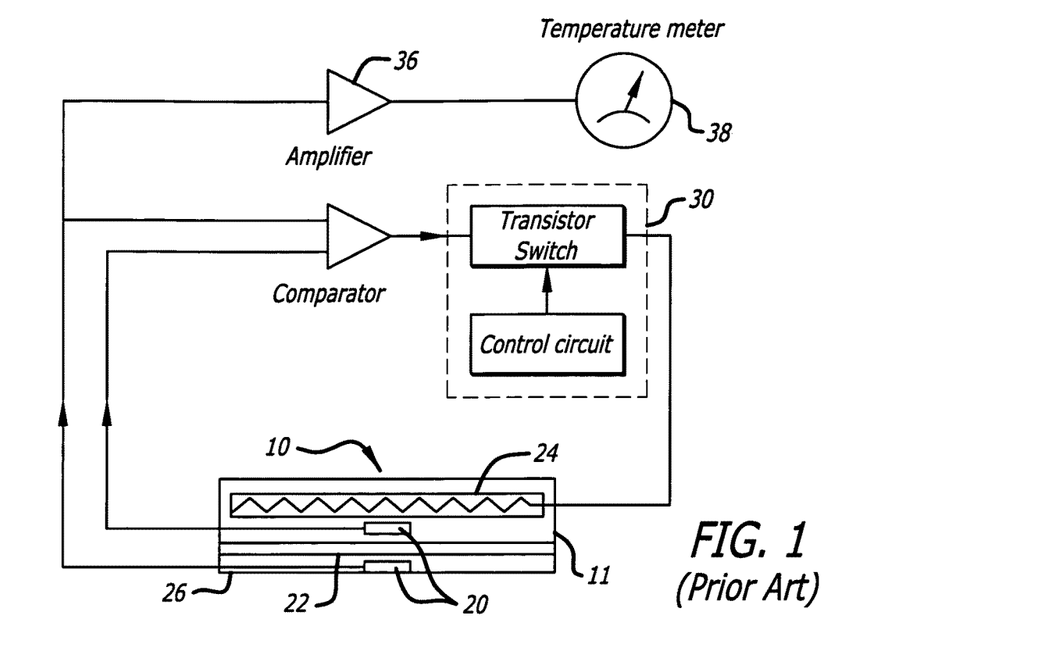
FIG. 1 is a schematic block diagram of a deep tissue temperature measurement system including a ZHF probe.

The thermocouples in the first support assembly embodiment illustrated in FIGS. 3-5 may be assembled with other elements of a DTT probe illustrated in FIG. 1, but the heater assembly is likely to become contaminated after use, and a disposable ZHF probe design is very desirable to avoid cross contamination between patients.

With reference to FIGS. 6-9, a second embodiment of a support assembly 500 for a DTT probe includes a heater integrated into the support assembly. There are no wires attached to this embodiment as both signal and power leads are available on a connector tab on the circumference of the assembly.

Figure 6:
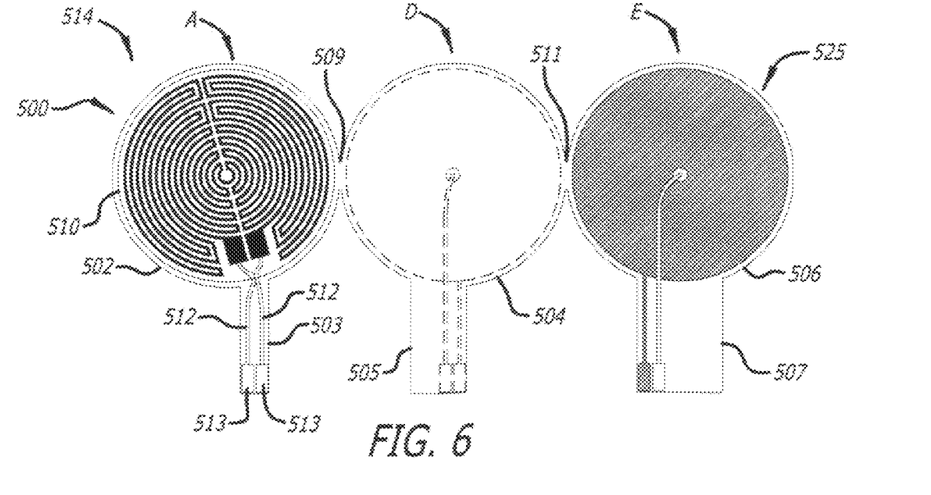
FIG. 6 is a drawing showing, in plan, a second thermal measurement support assembly embodiment for a ZHF probe constituted of a film of material including three sections joined by two hinges, in which the sections are opened and lie in the same plane with a first surface of the film visible.
Figure 7:
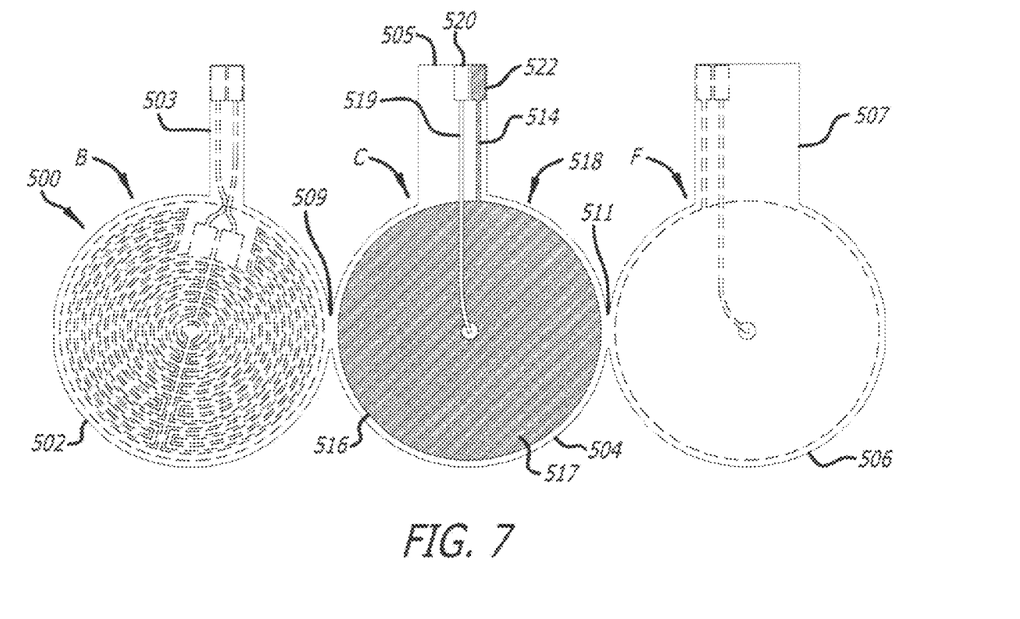
FIG. 7 is a drawing showing, in plan, the film of material of FIG. 6, in which the sections are opened and lie in the same plane with second surface of the film visible.

As best seen in FIGS. 6 and 7, the support assembly 500 includes a flexible substrate, preferably a sheet of flexible, thermally insulative material that is formed to include a plurality of contiguous sections. For example three contiguous paddle-shaped sections with disks 502, 504, and 506 of equal diameter are formed and aligned so that their centers lie on a straight line. Each disk transitions to a tab for supporting one or more electrical leads. The tabs are indicated by reference numerals 503, 505, and 507, respectively. The inner periphery of each disk is continuous with each adjacent inner periphery at a point that is tangent to the perimeter of the inner circle and which intersects the line upon which the centers are aligned. Thus, the inner periphery of the outer disk 502 is continuous with the periphery of the inner disk 504 at 509, and the inner periphery of the outer disk 506 is continuous with the periphery of the inner disk 504 at 511, which is diametrically opposite 509 on the periphery of the inner disk 504. Each disk has two opposite-facing, disk-shaped major surfaces. Thus, the outer disk 502 has major surfaces A and B, the inner disk 504 has major surfaces C and D, and the outer 506 has surfaces E and F. The major surfaces A, D, and E are on one side of the support assembly 500; the major surfaces B, C, and F are on the opposite side.

As seen in FIGS. 6 and 7, a heater 514 is formed on the major surface A by, for example, depositing a layer of copper on the surface and then etching the copper layer. The etching includes formation of leads 512 for the heater on the tab 503 that terminate in pins 513 at the outer edge of the tab 503. The etching also exposes a ring 510 of insulative material at the periphery of the major surface A. The layer 515 of copper on major surface C is etched to expose a ring 516 of insulative material at the periphery of the surface. The disk 517 of copper film inside the ring 516 is used as one element of a thermocouple 518. For example, the thermocouple 518 is fabricated by soldering, brazing, or welding one end of an insulated chromel wire 519 to the disk 517 of copper film, preferably, but not necessarily, at or near the center of the surface C. The other end of the chromel wire 519 is soldered, brazed, or welded to a chromel pin 520 mounted to the tab 505. Etching the copper on the major surface C also forms a lead 521 and a pin 522 for the copper portion of the thermocouple 518 on the tab 505. Another thermocouple 525 is similarly fabricated on the major surface E. Etching removes copper from the major surfaces B, D, and F so that those surfaces have no copper thereon.

Figure 8:
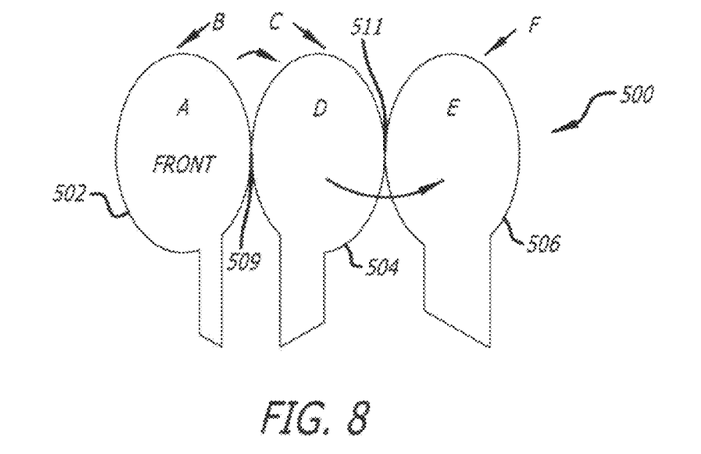
FIG. 8 is a perspective drawing of the film of material showing how the three sections are folded together.
Figure 9:
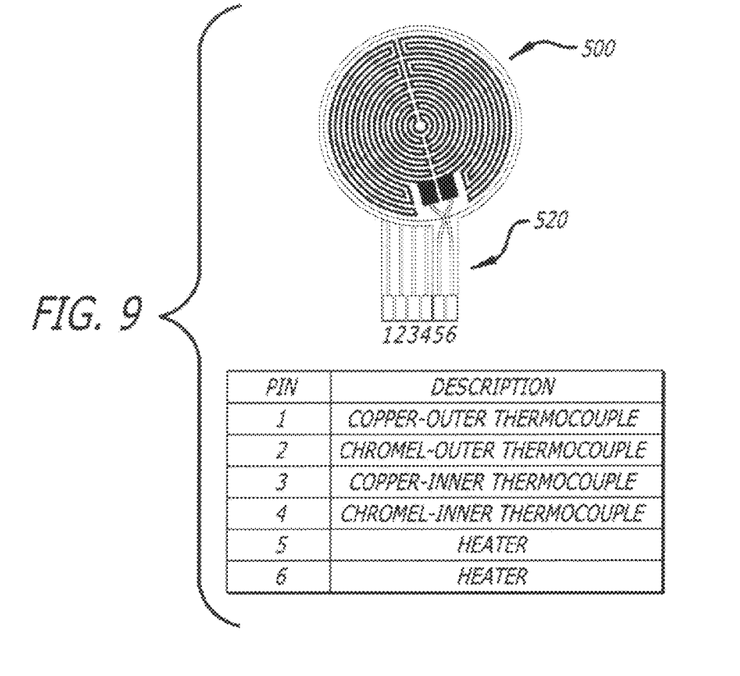
FIG. 9 is a drawing showing, in plan, the top side of an assembled DTT probe with the second support assembly embodiment. The figure includes a table illustrating assignment of pins of the probe.

With the heater 514 and thermocouples 518 and 525 thus formed, the support assembly 500 may be Z-folded as shown in FIG. 8. Preferably, the sections 502 and 504 are folded at 509 by swinging the major surfaces B and C together and the sections 504 and 506 are folded at 511 by swinging the major surfaces D and E together. The folded support assembly 500 is seen in the top plan view of FIG. 9. In this aspect, the support assembly 500 is preferably oriented with respect to a location on a body where a deep tissue temperature reading is to be taken by denominating the heater 514 as the top of the assembly, and major surface F as the bottom. In this aspect, the tabs 503, 505, and 507 are aligned by the folding place so as to align all of the leads and pins on a single side of a composite tab 520. Preferably, but not necessarily, the composite tab 520 is oriented with the aligned pins facing in the same direction as the heater on major surface A. The table in FIG. 9 sets forth the pin assignments. In the table, the lower thermocouple is on major surface E and the upper thermocouple is on major surface C. The connectors on the composite tab 520 provide electrical access to each of the thermal sensors and to the heater. A compression connector (not seen) may be received on the composite tab 520.

Figure 10:
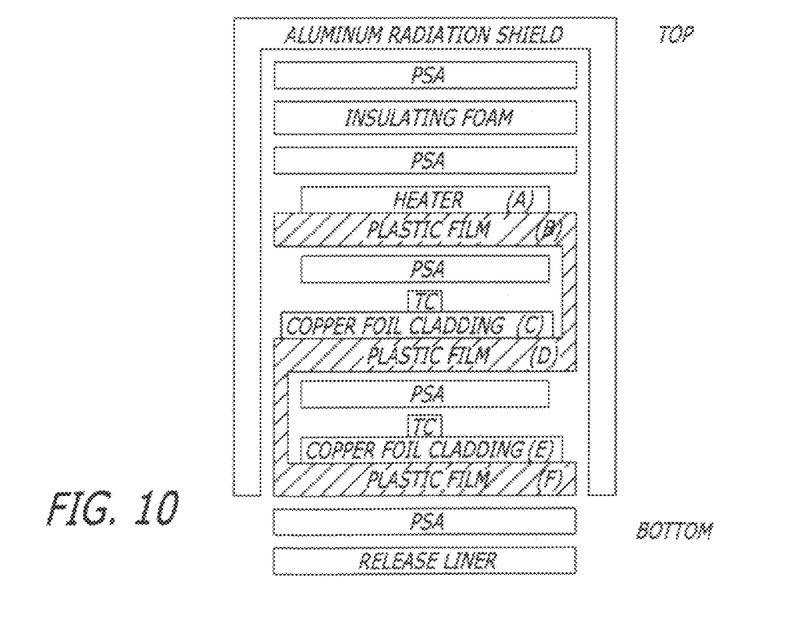
FIG. 10 is a sectional view in elevation showing the assembled DTT probe with the second support assembly embodiment.

Final assembly of a DTT probe construction with a support assembly 500 according to the second embodiment is illustrated in FIG. 10. In the unfolded assembly, there are three circular disks and six surface regions. Layers formed by folding the support assembly are labeled as shown in the figures. The layers are, as follows:

Major surface A is the electric heater
Major surface B is plastic film
Major surface C is a copper layer that supports a thermal sensor
Major surface D is a plastic film
Major surface E is a copper layer that supports a thermal sensor
Major surface F is plastic film The assembled DTT probe may include additional layers added to the structure of the probe during assembly. For example, layers of pressure-sensitive adhesive (PSA) 527 may be disposed between the folded sections and on the top and bottom major surfaces, an insulating layer may be disposed on the layer of PSA above the heater, and a further layer of PSA may be disposed on the top of the insulating layer. Further, a release liner may be provided on the bottom PSA layer, and an aluminum radiation shield may be supported on the top PSA layer. The exemplary embodiment of the DTT probe shown in FIG. 10, with the second support assembly embodiment, includes sixteen separate layers. The materials and constructions described for the support assembly and representative dimensions for the layers which are shown in Table I below illustrate the achievement of a disposable DTT probe with a very low vertical profile, an inexpensive construction, and a flexible structure that can adapt to differing contours of various measurement locations on the body of a person.

TABLE I

| Layer | Thickness (in.) (est.) |
| --- | --- |
| Aluminum foil radiation shield | 0.001 |
| Pressure-sensitive adhesive | 0.0005 |
| Insulating foam | 0.010 |
| Pressure-sensitive adhesive | 0.0005 |
| Heater - Surface A | 0.001 |
| Plastic film - Surface B | 0.002* |
| Pressure-sensitive adhesive | 0.0005 |
| Upper Thermocouple | 0.0005 |
| Metal foil (copper) - Surface C | 0.001 |
| Plastic film - Surface D | 0.002* |
| Pressure-sensitive adhesive | 0.0005 |
| Lower thermocouple | 0.0005 |
| Metal Foil (copper) - Surface E | 0.001 |
| Plastic film - Surface F | 0.002* |
| Pressure-sensitive adhesive | 0.0005 |
| Release liner | 0.001 |
| TOTAL | 0.0235 |

*This dimension is the thickness of the substrate, which may vary with the design goals of the DTT probe.

The second support assembly embodiment illustrated in FIGS. 6-10 may be assembled with other elements of a DTT probe system, as illustrated in FIG. 1.

FIGS. 11A, 11B, 12A, and 12B illustrate third and fourth support assembly embodiments. Each of the third and fourth embodiments is characterized by a structure with a single substrate layer formed into a plurality of contiguous sections that are separated into strata on which the thermal sensors are disposed in a spaced-apart relationship. Preferably, the thermal sensors are disposed on two contiguous elongate support members, disposed in a spaced-apart, an opposing or an adjacent relationship, inwardly of the periphery of the support assembly. Preferably, the substrate has the shape of an annulus with a circumferential heater disposed thereon and the two sensor support members projecting inwardly thereof and separated by a thermally insulating layer separate from the substrate. It is desirable to provide a lead support tab projecting outwardly of the annulus and supporting leads for the heater and the thermal sensors.

Figure 11A:
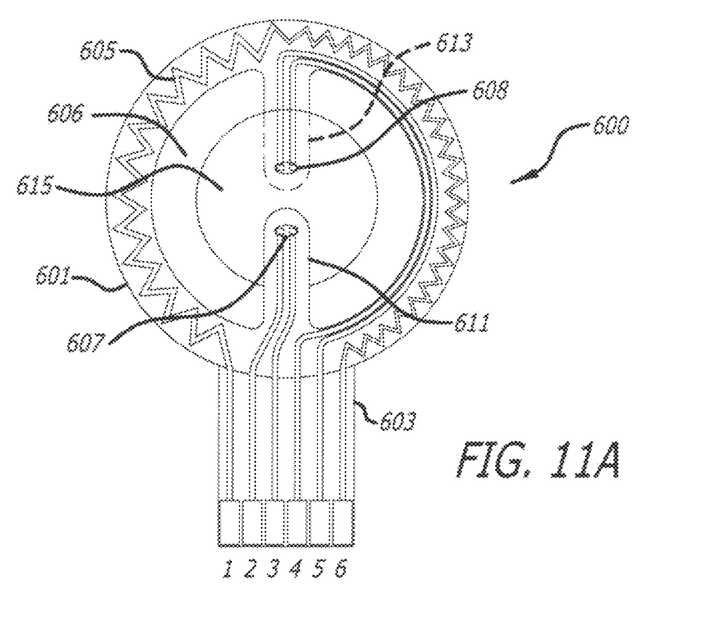
FIGS. 11A and 11B are plan and side views of a third support assembly embodiment.
Figure 11B:
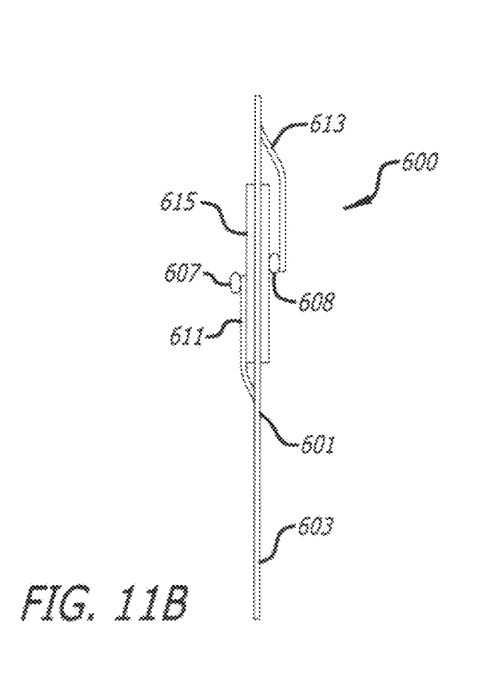

In FIGS. 11A and 11B, a two-sided, planar sheet 601 of flexible substrate material is provided and one side of the sheet is coated with a layer of conductive metal such as copper. The copper sheet is etched to form a heater 602, thermocouple traces, leads, and pins. Chromel traces, leads, and pins are deposited on the substrate, and a single paddle-shaped section with a disk 600 is formed by cutting, stamping or machining the planar sheet. The disk 600 transitions to a tab 603 for supporting the copper and chromel leads and pins. The heater 605 is defined along the circular circumference of the disk 600 by a conductive trace having a triangle wave shape. The heater 605 surrounds the thermocouple junctions 607 and 608. The thermocouple junctions 607 and 608 are aligned with respect to a diameter of the disk 600 and disposed on either side of its center. The inner section 606 of the substrate is die cut and removed leaving the heater 605 supported on an annulus of substrate material and the thermocouple junctions 607 and 608 disposed on two thermal sensor support tabs 611 and 613 that project inwardly of the annulus, in an opposing relationship. The two tabs 611 and 613 are then separated into strata and a film or layer 615 of thermally insulating material that is separate from the substrate is interposed therebetween, which produces a vertical separation, and inserts a thermal resistance, between the thermocouples. Assignments of the pins in FIG. 11A are given in Table II.

TABLE II

| PIN | DESCRIPTION |
|-----|-------------|
| 1 | HEATER |
| 2 | THERMOCOUPLE 607 |
| 3 | THERMOCOUPLE 607 |
| 4 | THERMOCOUPLE 609 |
| 5 | THERMOCOUPLE 609 |
| 6 | HEATER |

Figure 12A:
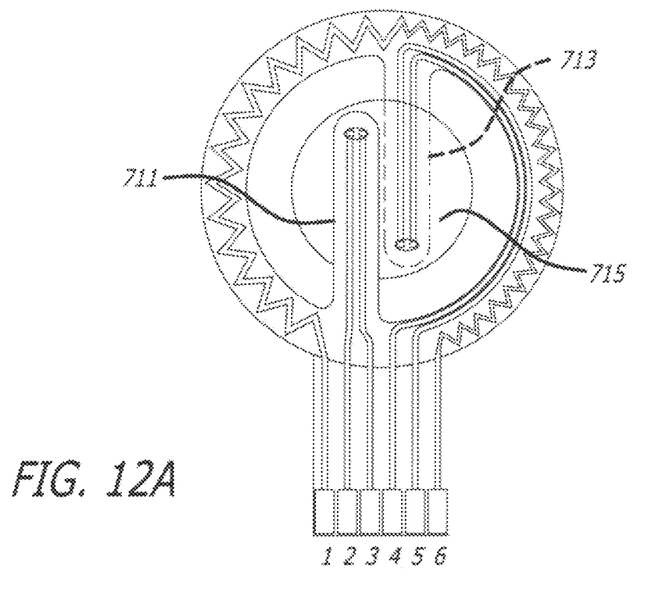
FIGS. 12A and 12B are plan and side views of a fourth support assembly embodiment.
Figure 12B:
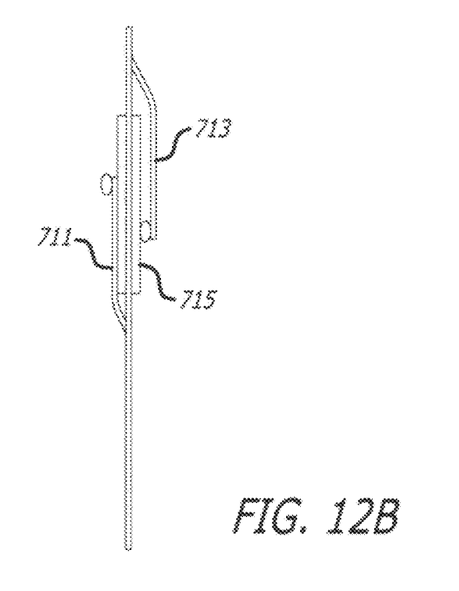

FIGS. 12A and 12B illustrate a fourth support assembly embodiment similar to the single-layer probe structure of the third embodiment seen in FIGS. 11A and 11B, but with elongated, oppositely-directed thermal sensor support tabs 711 and 713 offset in an adjacent relationship on respective sides of the diameter on which the tabs 611 and 613 are aligned. This arrangement allows a thicker layer 715 of thermally insulating material to be placed between the tabs. Thicker insulation decreases the sensitivity of the probe and increases the amplitude of the error signal. This is an advantage because it makes it easier to operate a control algorithm when zero-heat-flux conditions prevail. The disadvantage is that increased thermal resistance increases equilibration time. The pin assignments for the fourth embodiment correspond essentially to those of the third.

The two embodiments of FIGS. 11A, 11B, 12A, and 12B are for a sensor assembly. A DTT probe with either embodiment may be assembled into a construction with fewer layers than that disclosed in FIG. 10. The expected advantages of these embodiments are 1) ease of construction, 2) minimization of radial temperature differences, 3) minimization of materials, and 4) because each embodiment is based on a single layer, no folding of the substrate is required during assembly or operation, although steps of tab separation and insertion of a thermally insulating layer are necessary. Each of these designs is intended to be disposable; each is designed to use circumferential heating as opposed to full diametric heating.

A support assembly according to any of the four embodiments may be constructed using a substrate constituted of a single double-sided sheet of plastic film such as Kapton® polyimide, Kaptrex® polyimide, polyester or another film of flexible, thermally insulating material. The sheet may be coated on one or both sides with a copper film and various elements such as heaters, copper disks, and copper leads and pins may be made by photo-etching before the support assembly is folded or separated. The sheet may then be die-cut to the required shape and folded or separated as described above. Other metals with high thermal conductivities, like gold or aluminum, may also be used, although copper is preferred because it can form one half of a T-type thermocouple; however, other types of thermocouples are possible, and it may be possible to dispense with metal films altogether if other thermal sensors such as balanced RTD's, thermistors, and/or point junction thermocouples are used to measure temperature. Chromel traces and leads may be formed by deposition, or by peening.

A disposable DTT probe may be easily and inexpensively made using the support assembly construction embodiments described above. Disposability makes the commercialization of a DTT probe possible. Also, a single-use probe limits the potential for cross-contamination and makes it possible for more patients to benefit from perioperative temperature monitoring.

Thus, although the invention has been described with reference to the presently preferred embodiment, it should be understood that various modifications can be made without departing from the spirit of the invention. Accordingly, the invention is limited only by the following claims.

The invention claimed is:

1. A zero-heat-flux temperature probe comprising:
a two-sided substrate;
a heater disposed on the substrate;
a plurality of sections defined in the substrate, in which each section is joined to at least one adjacent section at a common peripheral location;
two thermal sensors, each of the two thermal sensors supported on a respective one of two adjacent sections;
the two adjacent sections folded together at a common peripheral location joining the two sections, wherein the folded two adjacent sections are in a stack configuration;
a thermal resistor disposed between the two thermal sensors; and
a lead support tab projecting outwardly of a periphery of one of the plurality of sections and
leads on the lead support tab for the heater and the thermal sensors,
wherein one of the plurality of sections has a generally round shape with the heater disposed thereon.

2. The zero-heat-flux temperature probe of claim 1, wherein the plurality of sections are the two adjacent sections, each of the two thermal sensors is mounted on a major support surface of a respective one of the two sections, and the sections are folded together in clam shell fashion such that the two thermal sensors face each other.

3. The zero-heat-flux temperature probe of claim 1, wherein the plurality of sections are three sections, each section has opposing major support surfaces, a first thermal sensor is mounted on a first major support surface of a first section of the two adjacent sections, the second thermal sensor is mounted on a second major support surface of the second section of the two adjacent sections, and the three sections are folded together such that the two thermal sensors face in the same direction.

4. The zero-heat-flux temperature probe of claim 3, wherein the heater is positioned to sandwich one of the two adjacent sections between the heater and the other of the two adjacent sections.

5. The zero-heat-flux temperature probe of claim 4, wherein the heater is supported on a major support surface of the third section.

6. A zero-heat-flux temperature probe comprising:
a sheet of flexible material with two sides;
a heater disposed on the sheet of flexible material;
two or more sections defined in the sheet;
two of the two or more sections joined at a peripheral location; two thermal sensors, each of the two thermal sensors supported on a respective one of the two or more sections;
the two of the two or more sections folded together at the peripheral location, wherein the folded two sections are in a stack configuration;
a thermal resistor disposed between the two thermal sensors; and
a lead support tab projecting outwardly of a periphery of the sheet of flexible material and leads on the lead support tab for the heater and the thermal sensors,
wherein one of the two or more sections has a generally round shape with the heater disposed thereon.

7. The zero-heat-flux temperature probe of claim 6, wherein each of the thermal sensors is a thermocouple.

8. The zero-heat-flux temperature probe of claim 7, wherein the two sections are folded together in clam shell fashion such that the thermal sensors are disposed in a stacked configuration.

9. A zero-heat-flux temperature probe comprising:
a flexible sheet of material with two sides;
a heater disposed on the flexible sheet of material;
at least three sections defined in the sheet;
each section joined to at least one adjacent section at a common peripheral location;
two thermal sensors, each of the two thermal sensors supported on a respective one of two adjacent sections;
the three sections folded together, wherein the folded three sections are in a stack configuration;
a thermal resistor disposed between the two thermal sensors; and
a lead support tab projecting outwardly of a periphery of the flexible sheet of material and leads on the lead support tab for the heater and the thermal sensors,
wherein one of the at least three sections has a generally round shape with the heater disposed thereon.

10. The zero-heat-flux temperature probe of claim 9, wherein each section has opposing major support surfaces, a first thermal sensor is mounted on a first major support surface of a first section of the two adjacent sections, the second thermal sensor is mounted on a second major support surface of the second section of the two adjacent sections, and the three sections are folded together such that the two thermal sensors face in the same direction.

11. The zero-heat-flux temperature probe of claim 10, wherein the heater is positioned to sandwich one of the two adjacent sections between the heater and the other of the two adjacent sections.

12. The zero-heat-flux of claim 11, wherein the heater is supported on a major support surface of the third section.

13. The zero-heat-flux temperature probe of claim 12, wherein the thermal sensors are thermocouples.

14. The zero-heat-flux temperature probe of claim 13, wherein each thermocouple includes a copper disk supported on a surface of a respective section and a chromel wire, wherein the copper disk is attached to the chromel wire at a thermocouple junction.

15. The zero-heat-flux temperature probe of claim 9, wherein the sheet is a flexible sheet of thermally insulating material.

16. The zero-heat-flux temperature probe of claim 15, wherein the sheet is coated with a copper film on each side.

17. The zero-heat-flux temperature probe of claim 16, wherein each copper film is etched to form an element of a respective one of the thermal sensors.

18. The zero-heat-flux temperature probe of claim 17, wherein the thermal sensors are thermocouples.

19. The zero-heat-flux temperature probe of claim 16, further comprising a heater positioned to sandwich one of the two thermal sensors between the heater and the other of the two thermal sensors.

20. The zero-heat-flux temperature probe of claim 19, wherein one copper film is etched to form the heater.

* * * * *